United States Patent
Salyer

(10) Patent No.: US 7,217,272 B2
(45) Date of Patent: May 15, 2007

(54) ORTHOPAEDIC ROTARY REAMER WITH IMPLANT COMPLIANT CUTTING TEETH

(75) Inventor: Paul E. Salyer, Warsaw, IN (US)

(73) Assignee: Symmetry Medical, Inc., Warsaw, IN (US)

( * ) Notice: Subject to any disclaimer, the term of this patent is extended or adjusted under 35 U.S.C. 154(b) by 165 days.

(21) Appl. No.: 10/721,809

(22) Filed: Nov. 25, 2003

(65) Prior Publication Data

US 2005/0113837 A1 May 26, 2005

(51) Int. Cl.
*A61B 17/00* (2006.01)

(52) U.S. Cl. ...................................... 606/80

(58) Field of Classification Search .................. 606/79, 606/80, 81
See application file for complete search history.

(56) References Cited

U.S. PATENT DOCUMENTS

| | | | | |
|---|---|---|---|---|
| 3,630,204 A | * | 12/1971 | Fishbein | 606/81 |
| 4,023,572 A | * | 5/1977 | Weigand et al. | 606/81 |
| 4,116,200 A | * | 9/1978 | Braun et al. | 606/81 |
| 5,100,267 A | * | 3/1992 | Salyer | 407/54 |
| 5,968,049 A | * | 10/1999 | Da Rold | 606/80 |
| 6,129,732 A | * | 10/2000 | Lechot | 606/80 |
| 2003/0181916 A1 | * | 9/2003 | Wolford | 606/81 |
| 2005/0075639 A1 | * | 4/2005 | Lechot | 606/81 |

FOREIGN PATENT DOCUMENTS

WO 03/059178 7/2003

* cited by examiner

*Primary Examiner*—Eduardo C. Robert
*Assistant Examiner*—James L. Swiger
(74) *Attorney, Agent, or Firm*—Taylor & Aust, P.C.

(57) ABSTRACT

An orthopaedic reamer for cutting bone includes a rotatable shaft and a cutting head coupled with the shaft. The cutting head includes a distal face with a radius and a plurality of cutting teeth. Each cutting tooth includes a pair of opposed side walls extending from the distal face and a cutting edge extending between the side walls. Each cutting edge includes at least three adjoining segments. Each segment has a radius which is less than the radius of the distal face.

16 Claims, 3 Drawing Sheets

ORTHOPAEDIC ROTARY REAMER WITH IMPLANT COMPLIANT CUTTING TEETH

BACKGROUND OF THE INVENTION

1. Field of the Invention

The present invention relates to orthopaedic reamers, and, more particularly, to orthopaedic reamers having a distal cutting face.

2. Description of the Related Art

An orthopaedic reamer is used to cut a bone and thereby form the bone with a predetermined shape for receiving an orthopaedic implant. For example, an intramedullary reamer may be placed into the intramedullary canal of the bone and used to ream the interior of the bone to receive the stem of an orthopaedic implant. Such a reamer includes a radial, peripheral surface which generally includes a plurality of radially extending teeth for cutting the bone in a radial direction as the reamer proceeds in an axial direction into the bone. The size of the opening formed in the bone is determined by the outside diameter of the reamer.

An orthopaedic reamer may also include a cutting head with a distal face which has a plurality of cutting teeth formed therein. The distal face has a shape which corresponds to the shape of an orthopaedic implant to be received within the bone, and includes a plurality of cutting teeth extending from the distal face. The reamer is placed against the bone surface to be cut, such as an acetabulum or glenoid, and is plunge cut into the bone. Such reamers are effective for removing a portion of the bone so that the bone is shaped to receive the implant.

An orthopaedic reamer including a distal face as described above may include cutting teeth which are formed by a punching operation for each individual tooth. Each cutting tooth typically includes a hole and a raised portion which extends from the distal face. The raised portion includes a humped or center portion which results in the bone being cut with an annular groove as the cutting head is rotated about its rotational axis. In other words, each cutting tooth includes a raised portion resembling half of a cone split longitudinally, with the base edge of the cone defining the cutting edge. Although such a cutting tooth configuration is effective to remove the bone for receiving an implant, the rough surface resulting from the cutting teeth may not be desirable for certain applications.

What is needed in the art is an orthopaedic reamer used for plunge cuts which effectively yet smoothly removes the bone.

SUMMARY OF THE INVENTION

The present invention provides an orthopaedic reamer including a cutting head with a plurality of cutting teeth, with each cutting tooth having a cutting edge at a substantially constant radius from the outside diameter of the shell.

The invention comprises, in one form thereof, an orthopaedic reamer for cutting bone, including a rotatable shaft and a cutting head coupled with the shaft. The cutting head includes a distal face with a radius and a plurality of cutting teeth. Each cutting tooth includes a pair of opposed side walls extending from the distal face and a cutting edge extending between the side walls. Each cutting edge includes at least three adjoining segments. Each segment has a radius which is less than the radius of the distal face.

An advantage of the present invention is that the configuration of the cutting teeth provides for a smoother cut of bone.

Another advantage is that the cutting teeth can be formed using a simple stamping operation.

Yet another advantage is that the cutting teeth are configured to cut the bone fast and smoothly.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
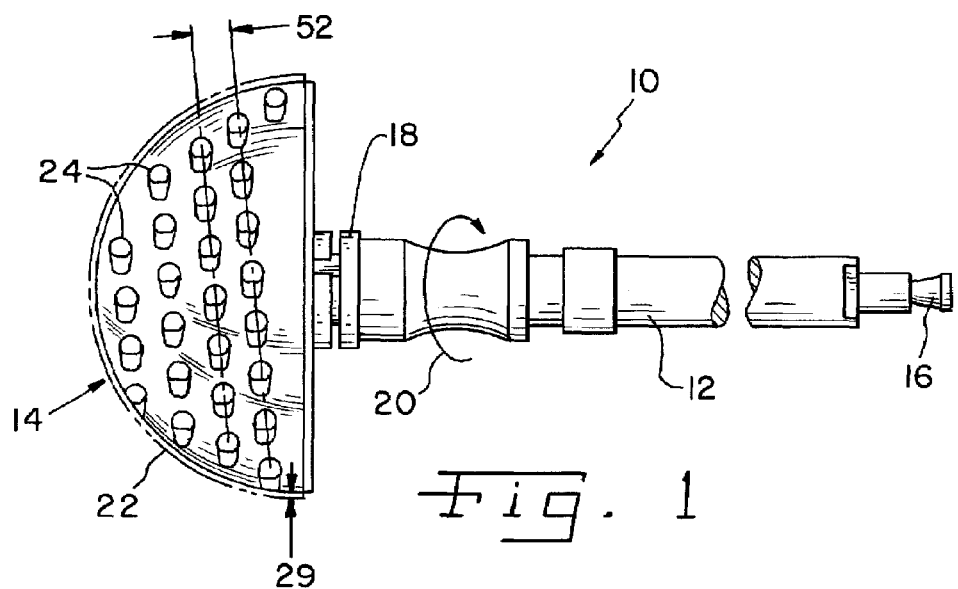
FIG. 1 is a side view of an embodiment of an orthopaedic reamer of the present invention.

Referring now to the drawings, there is shown an embodiment of an orthopaedic rotary reamer 10 of the present invention which is used for cutting bone. In the embodiment shown, orthopaedic reamer 10 is an acetabular reamer used to cut an acetabulum, but may also be configured to cut bone such as a shoulder or knee joint. Orthopaedic reamer 10 generally includes a shaft 12 and a cutting head 14.

Shaft 12 includes a driven end 16 and a distal end 18. Driven end 16 is removably coupled with a source of rotational power for rotatably driving shaft 12 in a driven direction, as indicated by arrow 20. Distal end 18 is coupled with head 14 in any suitable manner, such as welding, threaded engagement, twist and lock, bayonet fittings, etc.

Head 14 includes a distal face 22 which is placed against a bone to be cut, and includes a predetermined shape which is dependent upon a particular application. In the embodiment shown, distal face 22 has a generally hemispherical shape with a predetermined radius of curvature for cutting an acetabulum associated with a hip joint. The radius of curvature is typically between approximately 15 mm and 40 mm for preparing an acetabulum in a pelvic bone.

Head 14 also includes a plurality of cutting teeth 24 which are formed in distal face 22 by a punching operation. Cutting teeth 24, shown more particularly in FIGS. 3–5, have a common shape with a pair of opposed side walls 26, a cutting edge 28 and a ramped portion 30. It is possible to form a head 14 having cutting teeth 24 with different shapes on the same head and still stay within the scope of this invention. However, this is probably not likely because of additional costs associated with using different punching tools to form cutting teeth 24 in cutting head 14.

Figure 3:
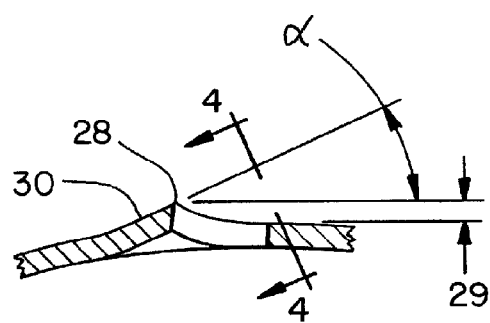
FIG. 3 is a side, sectional view of one of the cutting teeth shown in FIG. 1.
Figure 4:
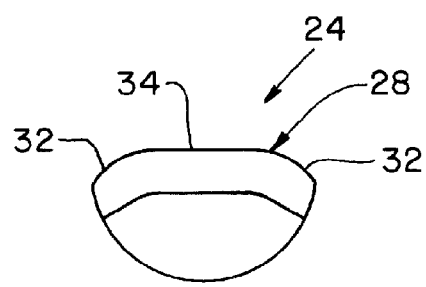
FIG. 4 is a sectional view taken along line 4—4 in FIG. 3.
Figure 5:
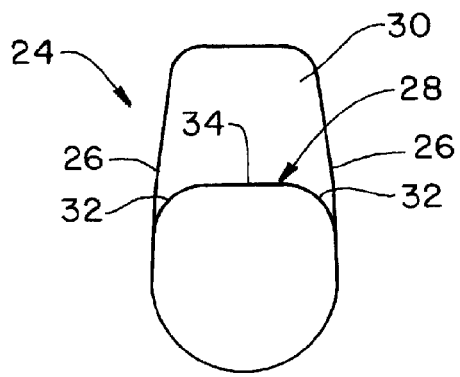
FIG. 5 is a plan view of the cutting tooth shown in FIGS. 3 and 4.

Referring now to FIGS. 3–5, a cutting tooth 24 of cutting head 14 shown in FIG. 1 will be described in more detail. Side walls 26 extend generally perpendicular from distal face 22 and generally parallel to each other. Side walls 26, however, may extend at another predetermined angle from distal face 22, or may be slightly curved rather than flat.

Cutting edge 28 extends between side walls 26 and defines the primary edge for removal of bone during a cutting operation. In the embodiment shown, cutting edge 28 extends from distal face 22 a distance 29 of approximately 0.020 inch. Cutting edge 28 includes at least two corner segments and at least one center segment extending between the corner segments. Each segment has a radius of curvature which is less than the radius of distal face 22 (e.g., between 14 mm and 39 mm). In the embodiment shown, cutting edge 28 includes two corner segments 32 and a single center segment 34. Center segment 34 has an inside radius of approximately 0.671 inch and an outside radius of approximately 0.684 inch. Corner segments 32 have an inside radius of approximately 0.045 inch and an outside radius of approximately 0.065 inch. It will be appreciated, however, that these dimensions are exemplary only and can vary from one size reamer to another, and from one application to another.

Ramped portion 30 extends between side walls 26, cutting edge 28 and distal face 22. Ramped portion 30 provides structural rigidity to cutting edge 28 and is configured to allow transport of bone chips to the interior of head 14 for collection and removal during operation. Ramped portion 30 is bent at a predetermined angle α relative to distal face 22. In the embodiment shown, ramped portion 30 is bent at an angle a of approximately 20° relative to distal face 22.

Figure 6:
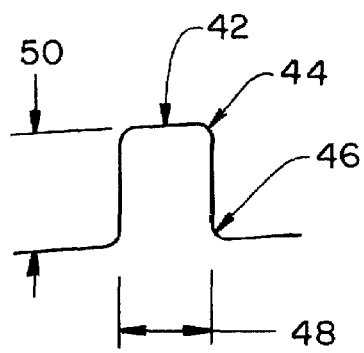
FIG. 6 is a side view of a punch tool used to form a cutting tooth shown in FIGS. 3–5.

FIG. 6 illustrates the details of one example of a punch 40 which may be used to form a cutting tooth 24 as described above. Punch 40 has a radius of curvature 42 of approximately 0.671 inch (corresponding to center segment 34); a radius of curvature 44 of approximately 0.045 inch (corresponding to corner segments 32); a radius of curvature 46 of approximately 0.062 inch (adjacent the juncture of side walls 26 and distal face 22); a dimension 48 of approximately 0.150 inch (corresponding to the width of a cutting tooth 24); and a dimension 50 of approximately 0.312 inch (corresponding to the height, plus a clearance distance, of a cutting tooth 24).

Figure 2:
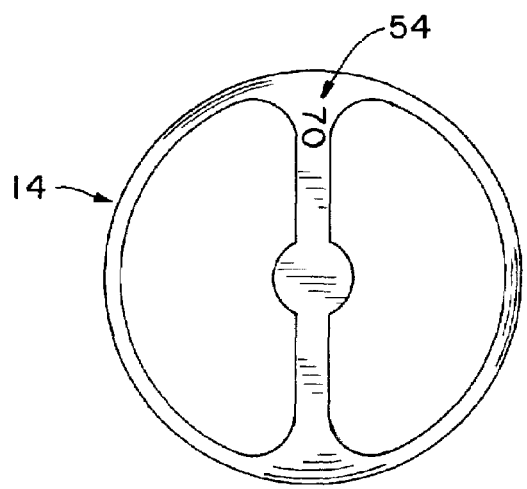
FIG. 2 is an end view of the cutting head of the orthopaedic reamer of FIG. 1.

During manufacture, cutting teeth 24 are formed in cutting head 14 using a punching operation. In the embodiment shown, cutting teeth 24 are placed in a spiral pattern on head 14 with a distance 52 between the rows of approximately 0.300 inch typical. For each cutting tooth, a hole is first punched or established using other appropriate processes such as laser cutting, etc. into cutting head 14. A portion adjacent the hole is then punched to define a cutting tooth 24 with side walls 26, cutting edge 28 and ramped portion 30. A size marking 54, such as the 70 mm diameter marking shown in FIG. 2, may be placed on the bridgeback portion of head 14. The bone may be cut smoothly using the plurality of cutting teeth 24.

During an orthopaedic operation, head 14 of orthopaedic reamer 10 is placed against a bone (not shown) to be cut. Orthopaedic reamer 10 is then driven in driven direction 20 using a rotating driver (not shown). As orthopaedic reamer 10 rotates, cutting teeth 24 cut the bone using the plurality of cutting teeth 24. When the bone is properly prepared for an implant, orthopaedic reamer 10 is removed.

Figure 7:
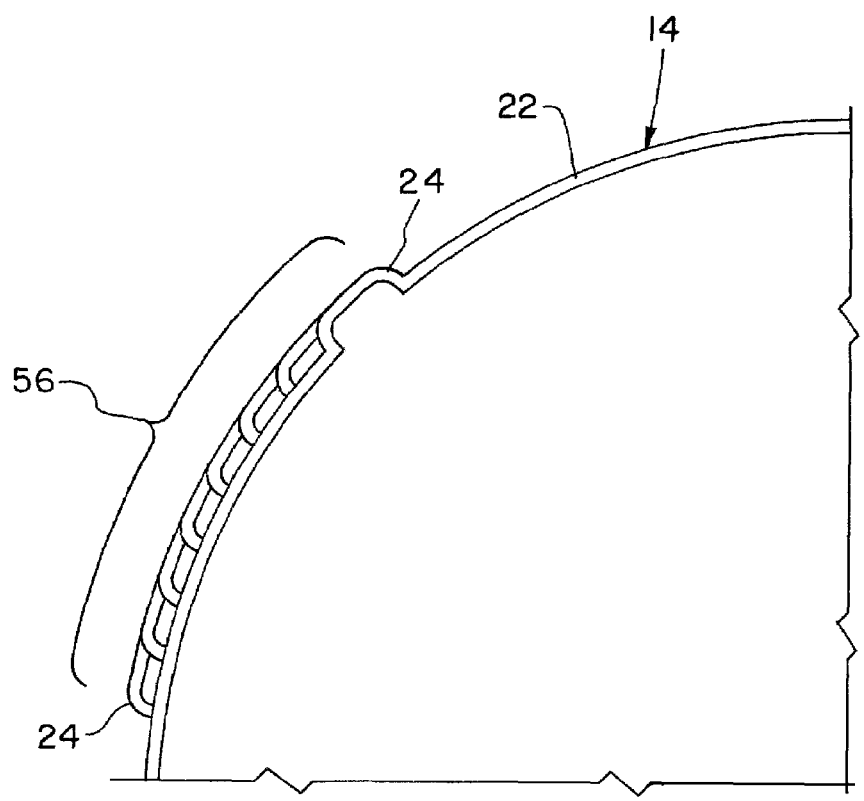
FIG. 7 is a graphical illustration of a cutting profile using a reamer of the present invention, as the reamer rotates through a given cutting area in a bone.

FIG. 7 is a graphical illustration of a cutting profile using reamer 10 of the present invention, as the reamer rotates through a given cutting area in a bone. In other words, using a tooth layout pattern as shown in FIG. 1 and tooth dimensions as described above, the individual cutting teeth 24 form an overlapped frontal profile as they rotate through a given cutting area. This cutting profile is at a substantially constant distance from distal face 22 of cutting head 14, which in turn results in a smoother cut profile 56 in a bone to be cut.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic reamer for cutting bone, comprising:
   a rotatable shaft; and
   a cutting head coupled with said shaft, said cutting head including a distal face with a radius and a plurality of cutting teeth, each said cutting tooth including a pair of opposed side walls extending from said distal face and a cutting edge extending between said side walls, each said cutting edge including two corner segments and at least one center segment extending between said corner segments, said center segments being positioned relative to each other to form a collective cutting profile at a substantially constant distance from said distal face of said cutting head, said collective cutting profile comprising each of said center segments of said plurality of cutting teeth.

2. The orthopaedic reamer of claim 1, wherein said at least one center segment includes a single center segment having a radius which is greater than a radius of said corner segments.

3. The orthopaedic reamer of claim 1, wherein said at least one center segment has a radius which is greater than a radius of said corner segments.

4. The orthopaedic reamer of claim 1, wherein said distal face has a radius of between approximately 15 mm and 40 mm, and each said segment has a radius of between approximately 14 mm and 39 mm.

5. The orthopaedic reamer of claim 1, wherein each said cutting tooth includes a ramped portion extending between said cutting edge and said distal face.

6. The orthopaedic reamer of claim 5, wherein said ramped portion also extends between said side walls.

7. The orthopaedic reamer of claim 1, wherein each said cutting tooth is formed using a punching operation.

8. The orthopaedic reamer of claim 1, wherein said distal face is generally hemispherical shaped.

9. A cutting head for an orthopaedic reamer, comprising a distal face with a radius and a plurality of cutting teeth, each said cutting tooth including a pair of opposed side walls extending from said distal face and a cutting edge extending between said side walls, each said cutting edge including two corner segments and at least one center segment extending between said corner segments, said center segments being positioned relative to each other to form a collective cutting profile at a substantially constant distance from said distal face of said cutting head, said collective cutting profile comprising each of said center segments of said plurality of cutting teeth.

10. The cutting head of claim 9, wherein said at least one center segment includes a single center segment having a radius which is greater than a radius of respective said corner segments.

11. The cutting head of claim 9, wherein said at least one center segment has a radius which is greater than a radius of said corner segments.

12. The cutting head of claim 9, wherein said distal face has a radius of between approximately 15 mm and 40 mm, and each said segment has a radius of between approximately 14 mm and 39 mm.

13. The cutting head of claim 9, wherein each said cutting tooth includes a ramped portion extending between said cutting edge and said distal face.

14. The cutting head of claim 13, wherein said ramped portion also extends between said side walls.

15. The cutting head of claim 9, wherein each said cutting tooth is formed using a punching operation.

16. The cutting head of claim 9, wherein said distal face is generally hemispherical shaped.

* * * * *